(12) United States Patent
Wu et al.

(10) Patent No.: US 7,964,370 B2
(45) Date of Patent: Jun. 21, 2011

(54) ANALYTICAL STRIP AND DETECTING METHOD USING THE SAME

(75) Inventors: Yi-Jen Wu, Hsinchu (TW); Wen-Pin Hsieh, Hsinchu (TW); Chih-Wei Hsieh, Hsinchu (TW)

(73) Assignee: Actherm Inc, Hsinchu (TW)

( * ) Notice: Subject to any disclaimer, the term of this patent is extended or adjusted under 35 U.S.C. 154(b) by 338 days.

(21) Appl. No.: 12/442,446

(22) PCT Filed: Oct. 17, 2008

(86) PCT No.: PCT/CN2008/001750
§ 371 (c)(1),
(2), (4) Date: Mar. 23, 2009

(87) PCT Pub. No.: WO2010/043075
PCT Pub. Date: Apr. 22, 2010

(65) Prior Publication Data
US 2010/0255512 A1    Oct. 7, 2010

(51) Int. Cl.
*G01N 33/53* (2006.01)
(52) U.S. Cl. ........... 435/7.91; 435/4; 435/7.5; 435/7.72; 435/7.9; 435/7.92; 435/7.93; 435/7.95; 435/28; 435/287.1; 435/287.7; 435/287.9; 435/817; 435/970; 435/975; 436/518; 436/528; 436/530; 436/808; 436/823
(58) Field of Classification Search .............. 435/4, 7.5, 435/7.72, 7.9, 7.91, 7.92, 7.93, 7.94, 7.95, 435/28, 287.1, 287.7, 287.9, 817, 970, 975; 436/518, 528, 530, 808, 823
See application file for complete search history.

(56) References Cited

U.S. PATENT DOCUMENTS

| 4,727,024 | A | * | 2/1988 | Koocher et al. ............. 435/7.4 |
| 4,828,801 | A |   | 5/1989 | Lombardy wife Alric et al. |
| 5,296,347 | A | * | 3/1994 | LaMotte, III ............... 435/5 |
| 5,308,775 | A | * | 5/1994 | Donovan et al. ............ 436/518 |
| 6,210,907 | B1 |  | 4/2001 | Cha |
| 6,478,938 | B1 |  | 11/2002 | Paek et al. |
| 6,670,115 | B1 |  | 12/2003 | Zhang |
| 6,756,019 | B1 |  | 6/2004 | Dubrow et al. |
| 7,455,816 | B2 |  | 11/2008 | Steuer et al. |

(Continued)

FOREIGN PATENT DOCUMENTS

CN    1139982 A    1/1997

(Continued)

OTHER PUBLICATIONS

U.S. Appl. No. 12/307,274, filed Jan. 1, 2009, Hsieh, Wen-Pin, et al.

(Continued)

*Primary Examiner* — Bao Thuy L Nguyen
(74) *Attorney, Agent, or Firm* — Ming Chow; Sinorica, LLC

(57) ABSTRACT

An analytical strip and a detecting method using the analytical strip are provided. The analytical strip includes a substrate having a channel thereon. The channel has a first region, a second region and a third region, which are connected sequentially. A first antibody is localized in the first region. A saccharide and a peroxidase are localized in the first or second region. A second antibody for recognizing a different epitope of an identical antigen with the first antibody is immobilized in the second region. An optical substrate and a substrate reagent including a saccharide oxidase are localized in the third region.

20 Claims, 10 Drawing Sheets

U.S. PATENT DOCUMENTS

| | | | |
|---|---|---|---|
| 2006/0188395 A1 | 8/2006 | Taniike et al. | |
| 2008/0019866 A1 | 1/2008 | Paek et al. | |
| 2008/0108096 A1 | 5/2008 | Ralph | |

FOREIGN PATENT DOCUMENTS

| | | | |
|---|---|---|---|
| CN | 1146557 A | 4/1997 | |
| CN | 1309294 A | 8/2001 | |
| CN | 1334924 A | 2/2002 | |
| CN | 1407339 A | 4/2003 | |
| CN | 1429337 A | 7/2003 | |
| CN | 1519563 A | 8/2004 | |
| CN | 1830390 A | 9/2006 | |
| CN | 1851459 A | 10/2006 | |
| CN | 1854728 A | 11/2006 | |
| CN | 1954214 A | 4/2007 | |
| CN | 2008001531 | 8/2008 | |
| CN | 2008001551 | 8/2008 | |
| CN | 2008001613 | 9/2008 | |
| CN | 2008001710 | 10/2008 | |
| CN | 2008001747 | 10/2008 | |
| CN | 101303358 A | 11/2008 | |
| JP | 2007139649 A | 6/2007 | |
| TW | 97135411 | 9/2008 | |
| TW | 97135929 | 9/2008 | |
| TW | 97137420 | 9/2008 | |
| TW | 97216918 | 9/2008 | |
| TW | 97217136 | 9/2008 | |
| TW | 97139296 | 10/2008 | |
| TW | 97139824 | 10/2008 | |
| TW | 97139825 | 10/2008 | |
| TW | 97218077 | 10/2008 | |
| TW | M350706 | 2/2009 | |
| TW | M354070 | 4/2009 | |
| TW | M359693 | 6/2009 | |
| WO | WO9008322 A1 | 7/1990 | |
| WO | WO0042434 A1 | 7/2000 | |
| WO | WO0184153 A1 | 11/2001 | |
| WO | WO2004086042 A1 | 10/2004 | |
| WO | WO2006047869 A1 | 5/2006 | |
| WO | WO 2006062312 | * | 6/2006 |
| WO | WO2007081330 A1 | 7/2007 | |
| WO | WO2007128286 A1 | 11/2007 | |
| WO | 2008001750 | 10/2008 | |

OTHER PUBLICATIONS

U.S. Appl. No. 12/306,972, filed Dec. 30, 2008, Hsieh, Chih-Wei et al.

U.S. Appl. No. 12/438,145, filed Feb. 20, 2009, Hsieh, Wen-Pin, et al.

U.S. Appl. No. 12/366,675, filed Feb. 6, 2009, Hsieh, Wen-Pin, et al.

* cited by examiner

ANALYTICAL STRIP AND DETECTING METHOD USING THE SAME

BACKGROUND OF THE INVENTION

1. Technical Field

The present invention relates to an analytical strip, and more particularly, to the analytical strip for quantitative assays of biological fluids.

2. Description of Related Art

Traditional quantitatively analytical assays utilize a unique capability possessed by the immunological molecules, which they can recognize as well as bind the biological molecules specifically. For example, the traditional enzyme linked immunosorbent assay (ELISA), which is typically conducted in a 96-well plate, characterizes in that determining concentration of an analyte (i.e., antigen) by the intensity of a detected signal resulted from the reaction between the analyte, the corresponding immunological molecules, the enzymes and the corresponding reagents. However, users usually need to perform a tedious washing step at every stage in the assay to wash away the non-binding and the non-specific binding molecules to prevent the assay from failure or in case that the false-positive results occur.

With the progress of technology, nowadays immunological analytical assays are carried out with the analytical strips which have microfluidic channels to simplify, or even omit, the complicated and repeated washing works traditionally required after every reaction stage of the assay. However, the known analytical strip, which is necessary to manually add reagents or substrates required for reactions into the analytical strip, causes inconvenience for the users. The reagents or substrates required for the conventional strips tend to degrade at room temperature or under light after long-term storage, which results in the errors of the assay. Accordingly, such reagents need to be stored in a specific condition, such as cooling or light-proof. Consequently, the conventional analytical strips are nevertheless inconvenient in use and storage.

In addition, conventional analytical strips with channels or micro-fluidic channels have other problems. While such a channel or micro-fluidic channel is typically bordered by a non-absorbent material, and the viscosity of the fluid sample to be analyzed is usually high for the sample is mainly composed of proteins or carbohydrates, part of the fluid sample tends to adhere to the surface of the channel and will not be reacted. Such scenario, if happens, will not only disadvantageously cause the waste of the fluid sample to be analyzed, but also will adversely affects the accuracy of quantifying assays.

In addition, the conventional analytical strip may facilitate the flow of the fluid sample by micro-fluidic channels so that the fluid sample will be delivered via the capillary force exerted by the structures of such channels to the reaction area. Another alternative approach to deliver the fluid sample involves applying a driving force, such as by a pressurizing means, at the time the fluid sample is introduced into the channel so that the fluid sample is propelled to the reaction area through the channel. However, either one of the aforementioned approaches tends to cause air bubbles occurring after the fluid sample is introduced into the channel. These bubbles, either large or small, will block the channel and result in inaccurate analyzing results.

SUMMARY OF THE INVENTION

To remedy the aforementioned shortcomings, the present invention discloses an analytical strip for quantitative assay of fluid samples. The analytical strip comprises a substrate having at least a channel thereon. The channel has a first region for receiving a fluid sample, a second region, and a third region. These three regions are arranged successively. In addition, the channel contains a first antibody, a saccharide, a peroxidase, a second antibody, an optical substrate and a substrate reagent. The first antibody is localized in the first region for recognizing an analyte in the fluid sample. The saccharide and the peroxidase may be localized in the first or the second region. The second antibody is immobilized in the second region for recognizing the same analyte as the first antibody does. Nevertheless, the second antibody and the first antibody are configured to recognize different epitopes of the analyte. Both the optical substrate and the substrate reagent that comprises a saccharide oxidase are localized in the third region. Upon introduction of the fluid sample into the channel, the first antibody, saccharide, and peroxidase will flow along with the fluid sample. Partial amount of the peroxidase, the first antibody and the analyte will together bind with the second antibody, and thus are retained in the second region. The unbound peroxidase will flow to the third region along with the fluid sample. The saccharide will be oxidized by the saccharide oxidase to produce hydrogen peroxide ($H_2O_2$). Afterward, the optical substrate and the produced hydrogen peroxide will be catalyzed by the peroxidase at the third region to generate an optical signal.

Hence, a primary object of the present invention is to provide an analytical strip that contains mostly reagents and materials required for reaction without intricate steps.

Another object of the present invention is to provide an analytical strip and mostly reagents and materials required for reaction contained therein are in a dry form so that the analytical strip can be stored for a relatively long period of time before use and preventing assay errors due to degradation of reagents.

The present invention also discloses a method for a quantitative assay. The method comprises following steps. (1) Providing a fluid sample that contains an analyte. (2) Providing a substrate. The substrate has at least one channel comprising a first region for receiving the sample, a second region for delivering the sample and a third region where the sample reacts. These three regions arranged successively. The substrate further comprises a first antibody, a saccharide, a peroxidase, a second antibody, an optical substrate and a substrate reagent. The first antibody is localized in the first region for recognizing the analyte in the fluid sample. The saccharide and the peroxidase may be localized in the first or the second region. The second antibody is immobilized in the second region for recognizing the analyte in the fluid sample. The second antibody and the first antibody are configured to recognize different epitopes of the identical analyte in the fluid sample. Both the optical substrate and the substrate reagent are localized in the third region, and the substrate reagent comprises a saccharide oxidase. (3) Introducing the fluid sample into the first region of the channel to allow the first antibody, saccharide, and peroxidase to flow along with the fluid sample. (4) Binding the analyte to the first antibody, the second antibody and partial amount of the peroxidase so as to be retained in the second region. The saccharide, the unbound first antibody, and the unbound peroxidase will flow to the third region along with the fluid sample so that the saccharide will be oxidized by the saccharide oxidase to produce hydrogen peroxide ($H_2O_2$). Then making the optical substrate react with the produced hydrogen peroxide, which is catalyzed by the peroxidase arriving at the third region, to generate an optical signal. And (5) detecting the generated optical signal.

Hence, another object of the present invention is to provide a method for a quantitative assay that uses an analytical strip containing mostly reagents and materials required for reaction so that a result of an assay could be obtained via directly detecting the reaction signal without intricate operation steps.

Another object of the present invention is to provide a method for a quantitative assay that uses a analytical strip wherein mostly reagents and materials required for reaction contained therein are stored in a dry form so that the analytical strip can be stored for a relatively long period of time before use and preventing assay errors due to degradation of reagents.

BRIEF DESCRIPTION OF THE DRAWINGS

The invention as well as a preferred mode of use, further objectives and advantages thereof will be best understood by reference to the following detailed description of illustrative embodiments when read in conjunction with the accompanying drawings, wherein.

DETAILED DESCRIPTION OF THE PREFERRED EMBODIMENTS

While the present invention proposes an analytical strip and a detecting method using the same, the physical and chemical principles of biological assay are known to one skilled in the art and need not be discussed at any length herein. Meanwhile, the accompanying drawings referred to in the following description are provided for illustrative purposes and need not to be made to scale.

Figure 1A:
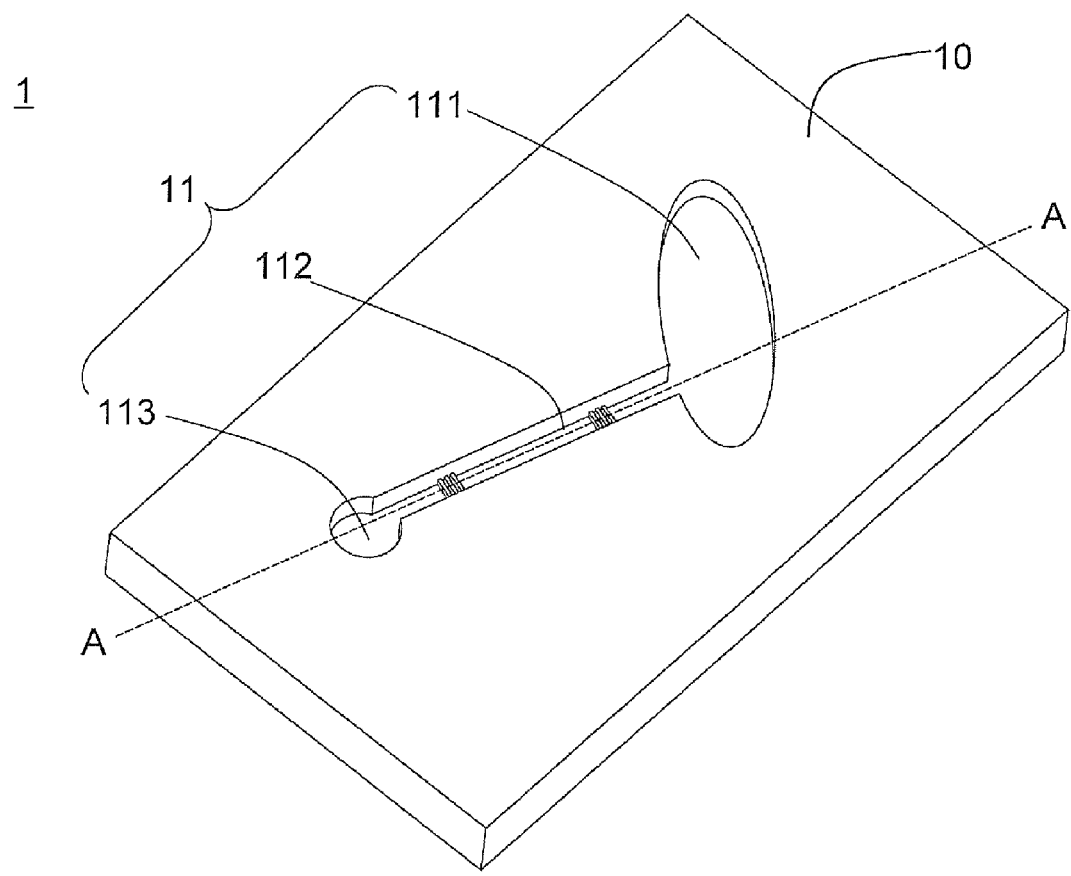
FIG. 1A is a perspective view of a analytical strip according to a first embodiment of the present invention.

Please refer to FIG. 1A for a perspective view of an analytical strip according to a first embodiment of the present invention. The analytical strip 1 comprises a substrate 10 having a channel 11 provided thereon. The channel 11 has a first region 111, a second region 112 and a third region 113. These three regions are arranged successively. The first region 111 is for a fluid sample to be introduced thereinto.

Figure 1B:
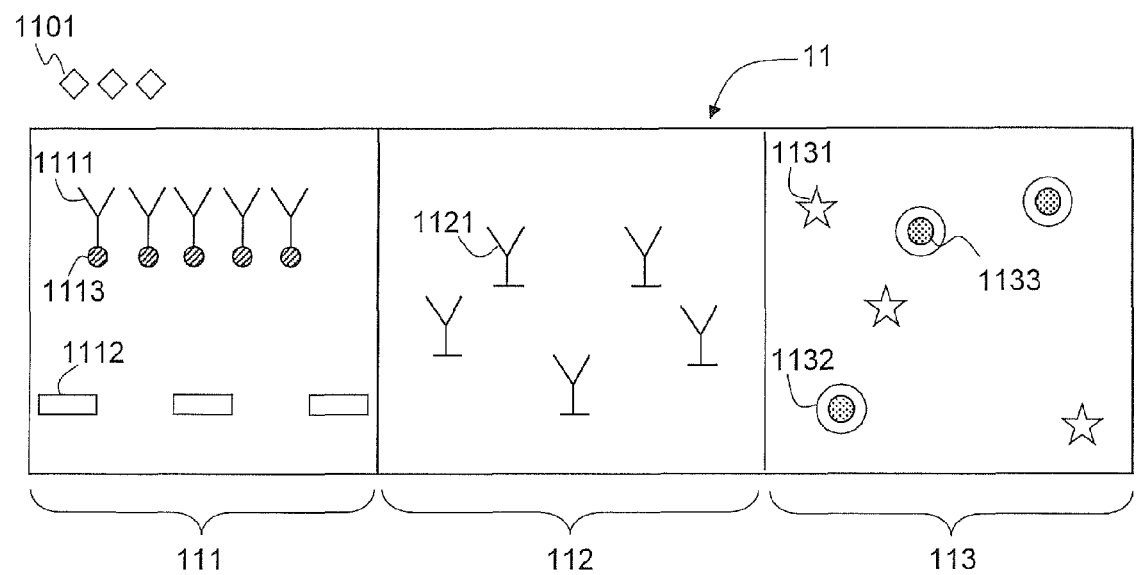
FIG. 1B is a schematic drawing showing distribution of reaction materials in a channel of the analytical strip of FIG. 1.

FIG. 1B is a schematic drawing showing distribution of reaction materials in the channel 11 of the analytical strip 1. The first region 111 contains a first antibody 1111, a saccharide 1112 and a peroxidase 1113. The second region 112 has a second antibody 1121 immobilized therein. The first antibody 1111 and the second antibody 1121 are configured to recognize different epitopes of an identical analyte 1101 in the fluid sample. Thus, both the first antibody 1111 and the second antibody 1121 could be either monoclonal antibodies (mAbs) or polyclonal antibodies (pAbs), as long as the first antibody 1111 and the second antibody 1121 will not compete with each other for the same antigen and thus interfere recognition of the antigen. In addition, the first antibody 1111 as well as the second antibody 1121 can be a whole antibody, an antigen binding fragment (Fab fragment), or in the form of a single-chain variable fragment (scFv). An optical substrate 1131 and a substrate reagent 1132 that comprises a saccharide oxidase 1133 are localized in the third region 113. The peroxidase 1113 can be a HRP (Horseradish Peroxidase), an AP (Ascorbate Peroxidase), or a hydrogen peroxidase. The optical substrate 1131 is preferable a 5-Amino-2,3-dihydro-1,4-phthalazinedione and the saccharide 1112 is preferable a glucose while the saccharide oxidase 1133 is glucose oxidase.

Figure 1C:
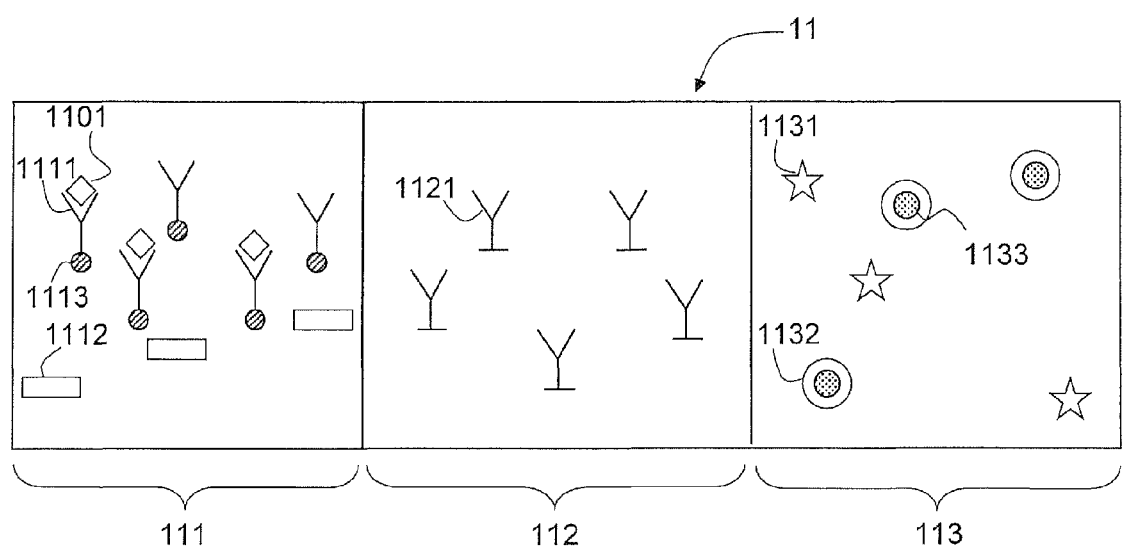
FIGS. 1C to 1E are schematic drawings showing variation of distribution of the reaction materials in the channel of the analytical strip of FIG. 1.
Figure 1D:
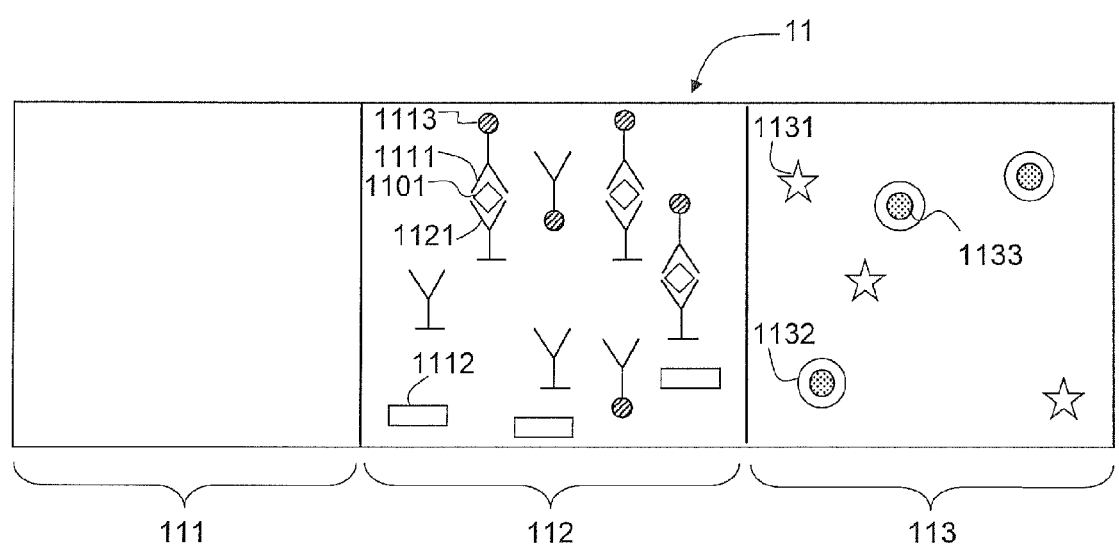
Figure 1E:
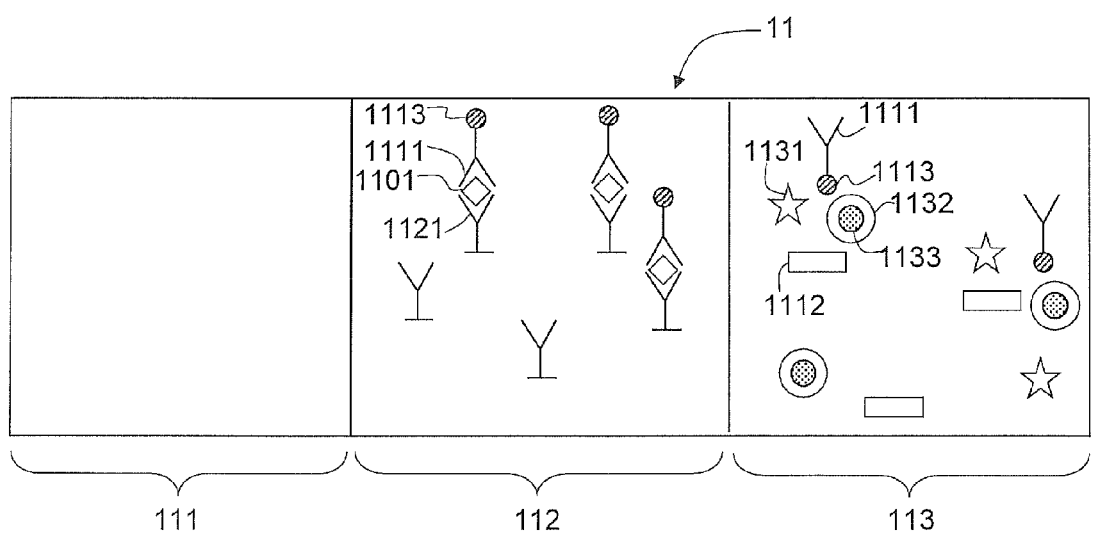

Please refer to FIGS. 1C through 1E that are, at the different reaction stages, schematic drawings showing the distribution of the reaction materials in the channel 11 of the analytical strip 1. In FIG. 1C, after the fluid sample containing the analyte 1101 is introduced into the channel 11, the first antibody 1111 recognizes and binds with the analyte 1101. Since the first antibody 1111, saccharide 1112, and peroxidase 1113 are not immobilized in the first region 111, the first antibody 1111, the analyte 1101 bound with the first antibody 1111, the peroxidase 1113, and the saccharide 1112 will flow along with the fluid sample toward the second region 112.

Referring to FIG. 1D, after the fluid sample arrives at the second region 112, the second antibody 1121 binds with the analyte 1101 and therefore a binding complex comprising the first antibody 1111, the analyte 1101 and the second antibody 1121 is formed. The second antibody 1121 is immobilized in the second region 112. Accordingly, the first antibody 1111 bound with the analyte 1101, the analyte 1101 bound with the second antibody 1121, and the peroxidase 1113 conjugating with the first antibody 1111, will be retained in the second region 112. Nevertheless, the saccharide 1112 that flows along with the fluid sample to the second region 112 keeps flowing along with the fluid sample, in company with the unbound first antibody 1111 as well as the peroxidase 1113 conjugating with the unbound first antibody 1111, toward the third region 113.

Now referring to FIG. 1E. The saccharide 1112, the unbound first antibody 1111, and the peroxidase 1113 conjugating with the unbound first antibody 1111, are now flowing to the third region 113. Then the saccharide 1112 reacts with the saccharide oxidase 1133 embedded in the third region 113, thereby producing hydrogen peroxide ($H_2O_2$). The resultant hydrogen peroxide and the optical substrate 1131 are catalyzed by the peroxidase 1113 that are now in the third region 113, so as to generate an optical signal. Consequently, by detecting the intensity of the generated optical signal, the concentration of enzyme involved in the reaction is thus determined. In other words, by detecting the intensity of the generated optical signal, the amount of the peroxidase 1113 arriving at the third region 113 and involving in the reaction can be determined. In addition, because the peroxidase 1113 is implemented as a constant amount in the analytical strip 1 during manufacture, it is easy to determine the amount of the peroxidase 1113 retained in the second region 112 after a simple subtraction ([The amount of the peroxidase 1113 retained in the second area 112]=[total amount of the peroxidase 1113]−[the amount of the peroxidase 1113 flowing to the third area 113]). At last, by using the amount of the peroxidase 1113 retained in the second region 112, it is possible to calculate the concentration of the analyte 1101 in the fluid sample, thereby achieving a quantitative assay.

Before reaction, the first antibody 1111 and the peroxidase 1113 are preferably directly conjugated with each other as depicted in FIG. 1B. Alternatively, the first antibody 1111 can conjugate with a Biotin whereas the peroxidase 1113 conjugate with an Avidin. Biotin and Avidin bind strongly to form an AB complex, during reaction, when first antibody 1111 is retained in the second region 112, it also draws some peroxidase 1113 to stay with it in the second region 112. The Avidin can be Avidin, Streptavidin or NeutrAvidin.

Figure 1F:
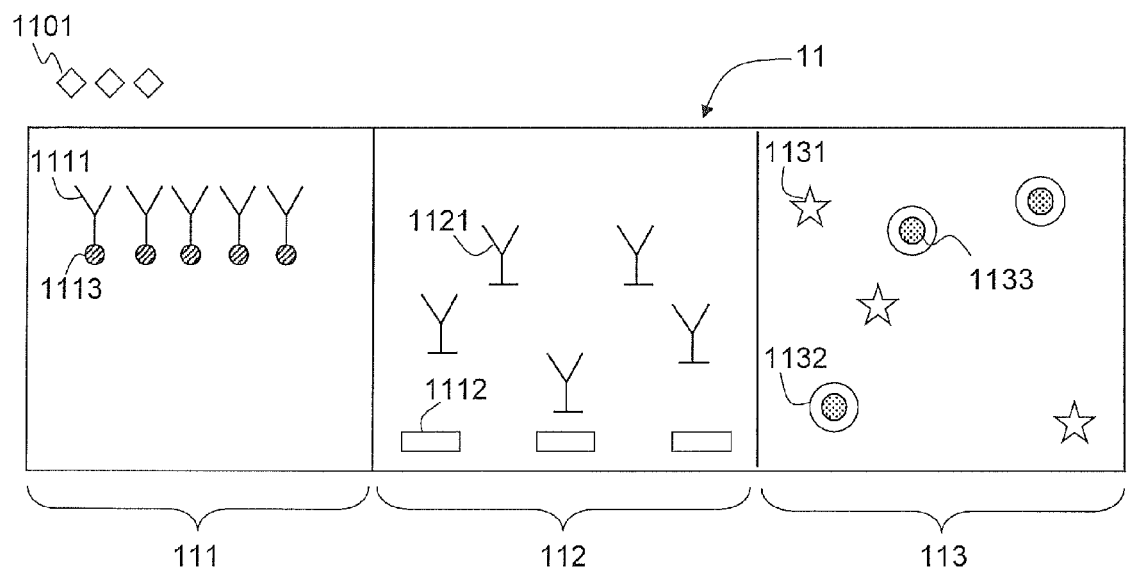
FIGS. 1F to 1H are schematic drawings showing alternative variation of distribution of the reaction materials in the channel of the analytical strip of FIG. 1.
Figure 1G:
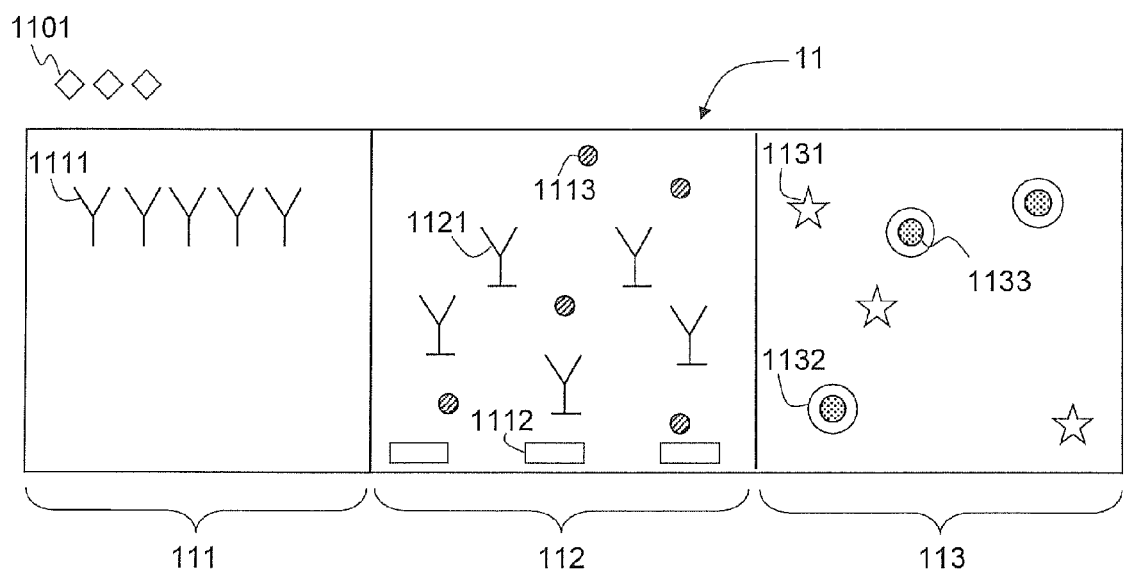
Figure 1H:
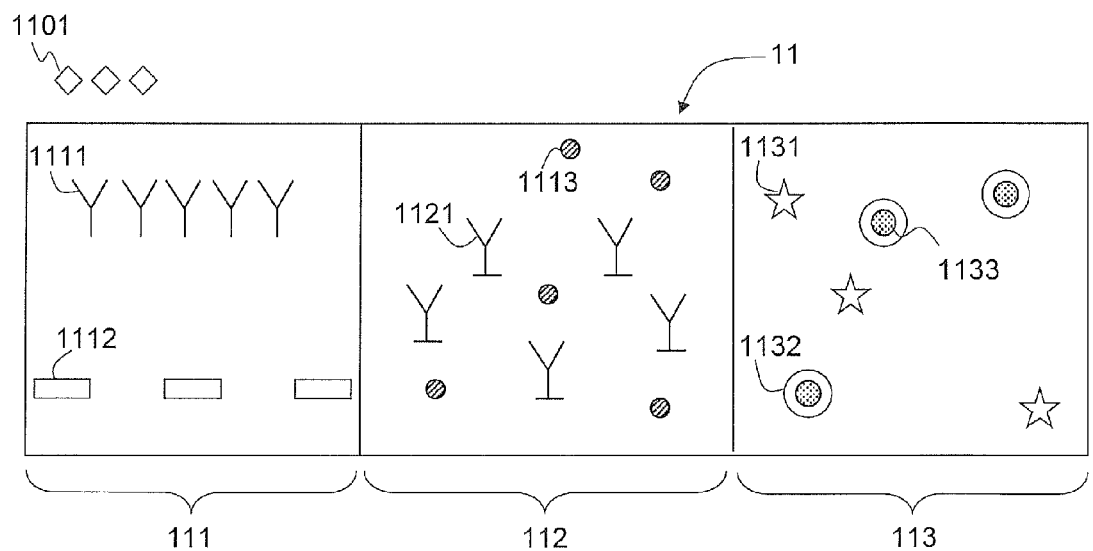

Then please refer to FIGS. 1F to 1H for schematic drawings showing other various modes of the distribution of the reaction materials in the channel 11 of the analytical strip 1 before reaction. According to the concept of the present invention, in the analytical strip 1, rather than disposing both the saccharide 1112 and peroxidase 1113 in the first region 111, the saccharide 1112 and peroxidase 1113 can both alternatively be disposed in the second region 112 as depicted in FIG. 1F.

In FIG. 1F, the first antibody 1111 and peroxidase 1113 are localized in the first region 111. The saccharide 1112 is localized in the second region 112. In the present mode, the first antibody 1111 and the peroxidase 1113 can directly conjugate with each other as described previously, or are respectively bound with the Biotin and the Avidin and to form an AB complex. The distribution of other reaction materials, such as the second antibody 1121, the optical substrate 1131, the substrate reagent 1132 and the saccharide oxidase 1133, is in the same manner as shown in FIG. 1B. By such configuration, after the fluid sample flows through the second region 112, the saccharide 1112 will also be brought to the third region 113 so as to enable the following reaction. The distribution of the reaction materials in different stages of reaction is as depicted in FIGS. 1C to 1E and needs not to be repeated.

Another mode of the distribution of the reaction materials is as depicted in FIG. 1G. The first antibody 1111 is localized in the first region 111 and the peroxidase 1113 and the saccharide 1112 are both localized in the second region 112. Still another mode of the distribution of the reaction materials is as depicted in FIG. 1H, the first antibody 1111 and the saccharide 1112 are localized in the first region 111 while the peroxidase 1113 is localized in the second region 112. Distributions of other reaction materials, of both modes described above, are in the same manner as shown in FIG. 1B, and the distribution of the reaction materials in different stages of reaction is as depicted in FIGS. 1C to 1E, so the repeated description is herein omitted.

Figure 1I:
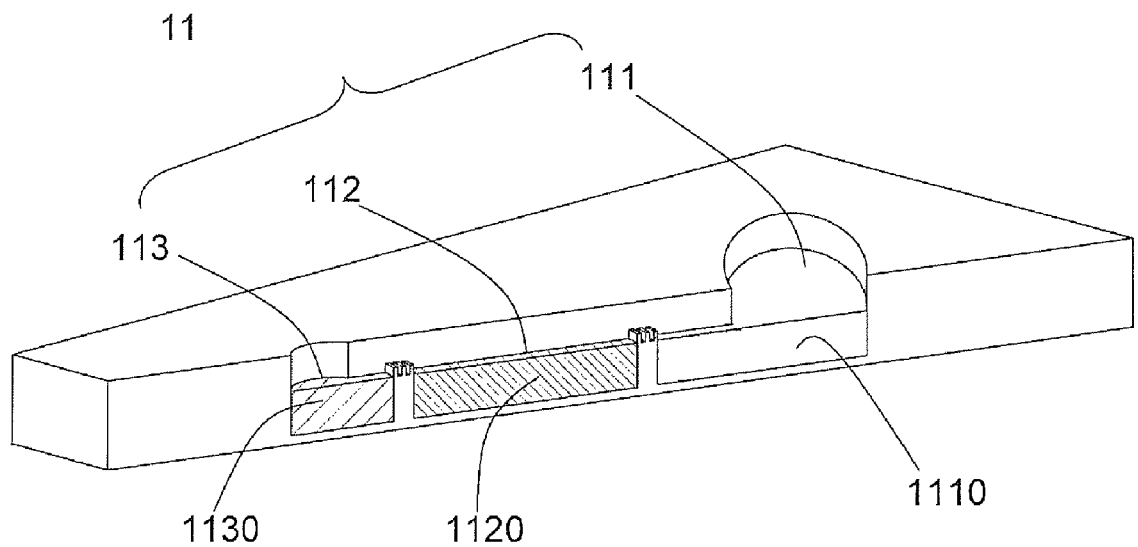
FIG. 1I is a sectional, perspective view of the analytical strip of FIG. 1.

Referring now to FIG. 1I, a sectional view of the analytical strip 1 is taken along line A-A in FIG. 1A. According to FIG. 1I, a fiber layer 1110 is provided at the bottom of the first region 111, and the first antibody (numbered as 1111 in FIG. 1B) is localized in the fiber layer 1110 so that after the fluid sample is introduced into the first region 111, the first antibody (numbered as 1111 in FIG. 1B) is brought by the fluid sample to the second region 112. A second nitrocellulose layer 1120 and a third nitrocellulose layer 1130 are provided respectively at the bottoms of the second region 112 and the third region 113. The second antibody (numbered as 1121 in FIG. 1B) is immobilized in the second nitrocellulose layer 1120 and the substrate reagent 1132 is embedded in the third nitrocellulose layer 1130.

The second nitrocellulose layer 1120 and the third nitrocellulose layer 1130 can be nitrocellulose membranes that are laminated at the bottoms of the second region 112 and the third region 113, respectively.

Another preferred approach to dispose the nitrocellulose layers at the bottoms of the second region 112 and the third region 113 is to cast a nitrocellulose solution at both bottoms of the second region 112 and the third region 113 followed by a drying process (air-drying or lyophilization). Accordingly, both the second nitrocellulose layer 1120 and the third nitrocellulose layer 1130 formed by such process, have hollow-matrix conformations. The channel 11 having nitrocellulose layers made by the casting process according to the present invention is different from the traditional micro-fluidic channel. In addition, in order to reduce the capillary force, each of the second region 112 and the third region 113 preferably has a width not less than 0.3 mm. The substrate 10 is preferable made of a biocompatible material. For optimising the result of the casting process, the channel 11 preferably has a surface roughness (Ra) ranging from 3 μm to 50 μm. The nitrocellulose layer 1120 preferably comprises an average thickness that equals to that of the nitrocellulose layer 1130. Moreover, the channel 11 may further comprise a fourth region (not shown) having a nitrocellulose layer that is formed at the bottom thereof and also has a hollow-matrix conformation for accommodating the excess fluid sample.

To prepare the nitrocellulose solution, nitrocellulose powder is mixed with a solvent containing esters and ketones. The volumetric ratio of the nitrocellulose powder to the solvent containing esters and ketones is preferably 1:9. Furthermore, when the nitrocellulose layer 1120 are formed by the casting process as described above, the second antibody 1121 is formed in the hollow-matrix conformation of the nitrocellulose layer 1120 by injecting a reaction solution containing the second antibody 1121 into the nitrocellulose layer 1120 followed by a drying process, and the second antibody 1121 is therefore left in the second nitrocellulose layer 1120 in a powder form.

In addition to the aforesaid approach that the second antibody 1121 is formed after the nitrocellulose layers are dried, an alternative approach is to firstly mix the solution comprising the second antibody 1121 with the nitrocellulose solution and then cast the mixed solution at the bottom of the second region 112 followed by a drying process. Thus, the second nitrocellulose layer 1120 is formed at the bottom of the second region 112 whereas the second antibody 1121 is left in the hollow-matrix conformation and dried to a powder form.

Similar approaches to providing the second nitrocellulose layer 1120 with the second antibody 1121 may be implemented to provide the third nitrocellulose layer 1130 with the substrate reagent 1132. The third nitrocellulose layer 1130 can be preformed followed by adding the substrate reagent 1132 thereinto, or the substrate reagent 1132 can be mixed with the nitrocellulose solution followed by applying the mixed solution onto the bottom of the third region 113, and thus the third nitrocellulose layer 1130 and substrate reagent 1132 is formed. Similar details are omitted herein.

In addition to the first embodiment described above, the present invention further provides a detecting method of fluid sample as a second embodiment. The analytical strip implemented in the second embodiment is substantially to the same as the analytical strip of the first embodiment, similar details will be omitted and all the reference numerals for indicating components of the analytical strip shall be referred to FIGS. 1B through 1H.

Figure 2:
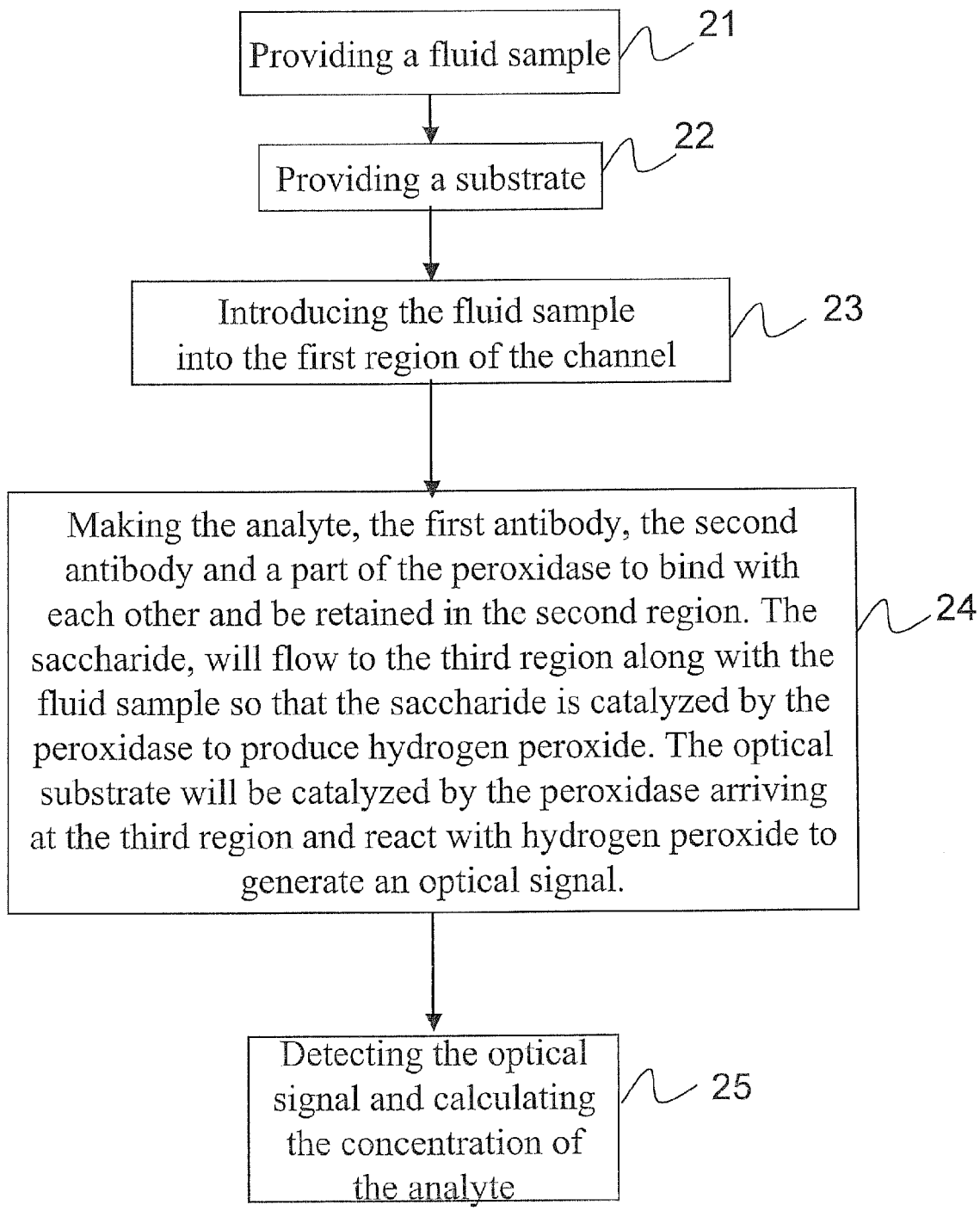
FIG. 2 is a flowchart of a detecting method according to a second embodiment of the present invention.

FIG. 2 is a flowchart of the detecting method according to the second embodiment of the present invention. The steps of the detecting method of the present invention are described as follows.

Step 21: Providing a fluid sample containing an analyte 1101 (as shown in FIG. 1B).

Step 22: Providing a substrate 10 having at least one channel 11 including a first region 111, a second region 112 and a third region 113 These three regions are arranged successively. The first region 111 is for the fluid sample to be introduced thereinto and has a first antibody 1111. The second region 112 has a second antibody 1121 immobilized therein. The first antibody 1111 and the second antibody 1121 are configured to recognize different epitopes of the analyte 1101 in the fluid sample. Thus, both the first antibody 1111 and the second antibody 1121 could be either monoclonal antibodies (mAbs) or polyclonal antibodies (pAbs), as long as the first antibody 1111 and the second antibody 1121 will not compete with each other for the same antigen and thus interfere recognition of the antigen. An optical substrate 1131 and a substrate reagent 1132 that comprises a saccharide oxidase 1133 are localized in the third region 113. The peroxidase 1113 can be a HRP (Horseradish Peroxidase), an AP (Ascorbate Peroxidase), or a hydrogen peroxidase. The optical substrate 1131 is preferable 5-Amino-2,3-dihydro-1,4-phthalazinedione and the saccharide 1112 is preferable a glucose while the saccharide oxidase 1133 is glucose oxidase. Besides, the saccharide 1112 and the peroxidase 1113 are distributed over the channel 11 in the same manner as described in the first embodiment (referring to FIGS. 1B, 1F, 1G and 1H).

Step 23: Introducing the fluid sample into the first region 111 of the channel 11 so that the fluid sample flows along the channel 11 through the first region 111, the second region 112 and the third region 113, successively, and thus brings the first antibody 1111, the saccharide 1112 and the peroxidase 1113 in the channel 11 to flow therewith.

Step 24: After introducing, the analyte 1101 will flow to the second region 112 along with the fluid sample. The second antibody 1121 will bind with the analyte 1101 and therefore a binding complex comprising the first antibody 1111, the analyte 1101 and the second antibody 1121 is formed. The second antibody 1121 is immobilized in the second region 112. Accordingly, the first antibody 1111 bound with the analyte 1101, the analyte 1101 bound with the second antibody 1121, and the peroxidase 1113 conjugating with the first antibody 1111, will be retained in the second region 112. Nevertheless, the fluid sample continuously brings the saccharide 1112, unbound first antibody 1111 and unbound peroxidase 1113 to the third region 113. In the third region 113, the saccharide 1112 is catalyzed by the saccharide oxidase 1133 to produce hydrogen peroxide. The optical substrate 1131 is catalyzed by the peroxidase 1113 arriving at the third region 113 and thus reacts with the hydrogen peroxide, so as to generate an optical signal.

Step 25: Detecting the optical signal generated in the Step 24. Consequently, the concentration of the enzyme involved in the reaction is determined by detecting the intensity of the generated optical signal. In other words, by detecting the intensity of the generated optical signal, the amount of the peroxidase 1113 arriving at the third region 113 and involving in the reaction can be determined. In addition, because the peroxidase 1113 is implemented as a constant amount in the analytical strip 1 during manufacture, it is easy to determine the amount of the peroxidase 1113 retained in the second region 112 after a simple subtraction ([The amount of the peroxidase 1113 retained in the second area 112]=[total amount of the peroxidase 1113]–[the amount of the peroxidase 1113 flowing to the third area 113]). At last, by using the amount of the peroxidase 1113 retained in the second region 112, it is possible to calculate the concentration of the analyte 1101 in the fluid sample, thereby achieving a quantitative assay.

According to the detecting method of the present invention, the preferable configuration of the first antibody 1111, the second antibody 1112 and the peroxidase 1113, the preferable categories of the first antibody 1111, the second antibody 1112 and the peroxidase 1113, the preferable structures of the regions of the channel 11, the configuration and the manufacturing method of the nitrocellulose layers, the composition and preferred ratio of the nitrocellulose solution, and the composition and manufacturing methods of the reaction materials are similar to those described in the first embodiment, and details thereof are omitted herein.

The present invention has been described by reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the concept of the present invention should be encompassed by the appended claims.

What is claimed is:

1. An analytical strip, comprising a substrate having at least one channel thereon, the channel having a first region, a second region and a third region that are arranged successively, the first region being used for a fluid sample to be introduced thereinto, the analytical strip being characterized by:
   a first antibody localized in the first region for recognizing an analyte in the fluid sample;
   a saccharide localized in the first or the second region;
   a peroxidase localized in the first or the second region;
   a second antibody immobilized in the second region for recognizing the analyte in the fluid sample, and the second antibody and the first antibody being configured to recognize different epitopes of the analyte in the fluid sample; and
   an optical substrate and a substrate reagent, both localized in the third region, wherein the substrate reagent comprises a saccharide oxidase;
   wherein upon introduction of the fluid sample containing the analyte into the channel, the first antibody, the saccharide, and the peroxidase flow along with the fluid sample, and then a part of the peroxidase binds with the first antibody, the analyte and the second antibody so as to be retained in the second region, allowing the other part of the peroxidase to flow along with the fluid sample to the third region, and then the saccharide arrives at the third region and is catalyzed by the saccharide oxidase so as to produce hydrogen peroxide, and then the optical substrate is catalyzed by the peroxidase arriving at the third region so as to react with the hydrogen peroxide and generate an optical signal.

2. The analytical strip of claim 1, wherein the first antibody and the peroxidase are localized in the first region and conjugate with each other.

3. The analytical strip of claim 1, wherein the first antibody further conjugates with a Biotin while the peroxidase conjugates with a molecule which is selected from the group consisting of Avidin, Streptavidin and NeutrAvidin.

4. The analytical strip of claim 1, wherein the peroxidase is selected from the group consisting of HRP (Horseradish Peroxidase), AP (Ascorbate Peroxidase), and hydrogen peroxidase.

5. The analytical strip of claim 1, wherein the optical substrate is 5-Amino-2,3-dihydro-1,4-phthalazinedione.

6. The analytical strip of claim 1, wherein the saccharide is glucose, and the saccharide oxidase is glucose oxidase.

7. The analytical strip of claim 1, wherein a fiber layer is provided at a bottom of the first region and the first antibody is embedded in the fiber layer.

8. The analytical strip of claim 1, wherein a nitrocellulose layer is provided at a bottom of each of the second and third regions, wherein the second antibody is immobilized in the nitrocellulose layer corresponding to the second region while the substrate reagent is embedded in the nitrocellulose layer corresponding to the third region.

9. The analytical strip of claim 8, wherein the nitrocellulose layer comprising a hollow-matrix conformation and is made by casting a nitrocellulose solution onto the bottoms of the second and third regions, followed by a drying process.

10. The analytical strip of claim 9, wherein each of the second region and the third region has a width of at least 0.3 mM.

11. A detecting method, comprising steps of:
providing a fluid sample that contains an analyte;
providing a substrate having at least one channel having a first region, a second region and a third region that are arranged successively, and the first region being used for the fluid sample to be introduced thereinto, and the substrate further comprises:
  a first antibody, localized in the first region for recognizing the analyte in the fluid sample,
  a saccharide localized in the first or the second region;
  a peroxidase localized in the first or the second region;
  a second antibody immobilized in the second region for recognizing the analyte in the fluid sample, wherein the second antibody and the first antibody are configured to recognize different epitopes of the analyte; and
  an optical substrate and a substrate reagent both localized in the third region, and the substrate reagent comprising a saccharide oxidase;
introducing the fluid sample into the first region of the channel to allow the first antibody, saccharide, and peroxidase to flow along with the fluid sample;
the analyte, the first antibody, the second antibody and a part of the peroxidase binding with each other and retaining in the second region;
the saccharide, the unbound first antibody, and the other part of the peroxidase unbound to flow to the third region along with the fluid sample so that the saccharide is catalyzed by the saccharide oxidase to produce hydrogen peroxide;
then making the optical substrate to be catalyzed by the peroxidase arriving at the third region and react with hydrogen peroxide to generate an optical signal; and
detecting the generated optical signal.

12. The detecting method of claim 11, wherein the first antibody and the peroxidase are localized in the first region and conjugate with each other.

13. The detecting method of claim 11, wherein the first antibody further conjugates with a Biotin while the peroxidase conjugates with an Avidin, wherein the Avidin is selected from the group consisting of Avidin, Streptavidin and NeutrAvidin.

14. The detecting method of claim 11, wherein the peroxidase is selected from the group consisting of HRP (Horseradish Peroxidase), AP (Ascorbate Peroxidase), and hydrogen peroxidase.

15. The detecting method of claim 11, wherein the optical substrate is 5-Amino-2,3-dihydro-1,4-phthalazinedione.

16. The detecting method of claim 11, wherein the saccharide is glucose, and the saccharide oxidase is glucose oxidase.

17. The detecting method of claim 11, wherein a fiber layer is provided at a bottom of the first region and the first antibody is embedded in the fiber layer.

18. The detecting method of claim 11, wherein a nitrocellulose layer is provided at a bottom of each of the second and third regions, and the second antibody is immobilized in the nitrocellulose layer of the second region whereas the substrate reagent is embedded in the nitrocellulose layer corresponding to the third region.

19. The detecting method of claim 18, wherein the nitrocellulose layer comprising a hollow-matrix conformation and is made by casting a nitrocellulose solution onto the bottoms of the second and third regions, followed by a drying process.

20. The detecting method of claim 19, wherein each of the second region and the third region has a width of least 0.3 mm.

* * * * *